United States Patent [19]

Kulprtahipanja

[11] Patent Number: 4,902,829

[45] Date of Patent: Feb. 20, 1990

[54] PROCESS FOR THE ADSORPTIVE SEPARATION OF HYDROXY PARAFFINIC DICARBOXYLIC ACIDS FROM OLEFINIC DICARBOXYLIC ACIDS

[75] Inventor: Santi Kulprtahipanja, Hoffman Estates, Ill.

[73] Assignee: UOP, Des Plaines, Ill.

[21] Appl. No.: 272,042

[22] Filed: Nov. 16, 1988

[51] Int. Cl.$^4$ .............................................. C07C 51/42
[52] U.S. Cl. ..................................... 562/580; 562/582; 562/593
[58] Field of Search ......................... 562/580, 582, 593

[56] References Cited

U.S. PATENT DOCUMENTS

| | | | |
|---|---|---|---|
| 2,985,589 | 5/1961 | Broughton et al. | 210/34 |
| 3,371,112 | 2/1968 | Winstrom et al. | 560/582 |
| 3,391,187 | 7/1968 | Cullen, Jr. et al. | 560/582 |
| 3,983,170 | 9/1976 | Sumikawa et al. | 560/582 |
| 4,772,749 | 9/1988 | Karrenbauer | 562/580 |

Primary Examiner—Werren B. Lone
Assistant Examiner—Vera C. Clarke
Attorney, Agent, or Firm—Thomas K. McBride; John F. Spears, Jr.; Jack H. Hall

[57] ABSTRACT

A process for the separation of one or more hydroxy paraffinic dicarboxylic acids from a feed mixture comprising said acid(s), and one or more olefinic dicarboxylic acids which process employs an adsorbent comprising a non-zeolitic, hydrophobic, crystalline silica molecular sieve material, to selectively reject the hydroxy paraffinic dicarboxylic acid(s) to a raffinate stream for the ultimate recovery of a purified quantity of such acid(s). The olefinic dicarboxylic acid(s) are thereafter removed from the adsorbent by contacting the adsorbent with a desorbent material and said acid(s) is (are) recovered to an extract stream. In a preferred embodiment the process uses a silicalite adsorbent, aqueous acetone desorbent and a simulated moving-bed countercurrent flow system utilizing therein a pre-pulse technique.

19 Claims, 4 Drawing Sheets

PROCESS FOR THE ADSORPTIVE SEPARATION OF HYDROXY PARAFFINIC DICARBOXYLIC ACIDS FROM OLEFINIC DICARBOXYLIC ACIDS

BACKGROUND OF THE INVENTION

The field of art to which the claimed invention pertains is adsorptive separation. More specifically, the invention relates to a process for separating hydroxy paraffinic dicarboxylic acids from a feed mixture comprising hydroxy paraffinic dicarboxylic acids and olefinic dicarboxylic acids which process employs a particular non-zeolitic, hydrophobic, crystalline silica molecular sieve adsorbent material to selectively reject and recover the hydroxy paraffinic dicarboxylic acids from the feed. In addition the process of the invention may preferably employ a means to enhance the selective adsorption of the extract components in the adsorption zone consisting of the introduction of an unadsorbed material into the adsorption zone of the process, such means being hereinbelow referred to as a "pre-pulse technique".

One commercially important hydroxy paraffinic dicarboxylic acid is malic acid. Malic acid occurs naturally in certain fruits, is the predominant acid in apples and is recoverable therefrom. Malic acid may also be synthesized by the hydrolysis of maleic acid. Unfortunately, the hydrolyzate not only contains malic acid, but also contains minority components comprising olefinic dicarboxylic acids such as unreacted maleic acid and a chemical intermediate, fumaric acid.

Substantial use of malic acid is made in the food industry as an acidulant, as an alternative to other materials such as citric acid. Malic acid is slightly less soluble than citric acid, when used as an acidulant, but it exhibits a stronger apparent acid taste which peaks more slowly thereby more effectively masking aftertastes. Malic acid is most commonly used in soft drinks, dry mix beverages, puddings, jellies and fruit fillings. Additionally, malic acid's melting point (129° Celsius) is lower than that of citric acid and, as a result, is more preferably utilized in the production of hard candies. It is known that at temperatures above about 100° to 150° Celsius, malic acid slowly dehydrates and reverts to fumaric acid. Although fumaric acid is likewise useable as an acidulant, its aqueous solubility is poorer than that of malic acid. Correspondingly, maleic acid, although used in the food industry as a preservative for fats and oils, is moderately toxic and is a strong irritant to tissue. Therefore, the removal of maleic acid and fumaric acids from the hydrolysis reaction product mixture produces a superior malic acid product.

It is therefore an object of the present invention to provide a process for the separation of commercially important hydroxy paraffinic dicarboxylic acids, such as malic acid, from a commercially available feed mixture comprising hydroxy paraffinic and olefinic dicarboxylic acids. In the preferred embodiment, the feed mixture is derived from the hydrolysis reaction of maleic acid and comprises a mixture of fumaric, malic and maleic acids, the adsorbent comprises silicalite, the desorbent comprises aqueous acetone and the process is carried out in a simulated countercurrent moving bed system using a pre-pulse technique.

DESCRIPTION OF THE PRIOR ART

Various methods of obtaining purified malic acid are known to the prior art. For example, U.S. Pat. No. 3,371,112, issued to Winstrom et al, teaches a means to purify malic acid using a weakly basic anion-exchange resin. Additionally, U.S. Pat. No. 3,391,187, issued to Cullen Jr., et al, teaches a two-stage crystallization process for the removal of maleic and fumaric acids from a mixture comprising such acids and malic acid. Likewise, in U.S. Pat. No. 3,983,170, Sumikawa et al teaches the use of a strongly basic anion exchange resin and in U.S. Pat. No. 4,772,749, Karrenbauer et al teaches the use of an elevated temperature and cationic exchange resin.

It is well known in the separation art that certain crystalline aluminosilicates can be used to separate one hydrocarbon type from another hydrocarbon type. The separation of normal paraffins from branched chain paraffins, for example, can be accomplished by using a type A zeolite which has pore openings from 3 to about 5 Angstroms. Such a separation process is disclosed in U.S. Pat. Nos. 2,985,589 to Broughton et al, and No. 3,201,491 to Stine. These adsorbents allow a separation based on the physical size differences in the molecules by allowing the smaller or normal hydrocarbons to be passed into the cavities within the zeolitic adsorbent while excluding the larger or branched chain molecules.

In addition to being used in processes for separating hydrocarbon types, adsorbents comprising type X or Y zeolite have also been employed in processes to separate individual hydrocarbon isomers. In the processes described, for example, in U.S. Pat. Nos. 3,626,020 to Neuzil, 3,663,638 to Neuzil, 3,665,046 to deRosset, 3,668,266 to Chen et al, 3,686,343 to Bearden Jr. et al, 3,700,744 to Berger et al, 3,894,109 to Rosback and 3,997,620 to Neuzil, particular zeolitic adsorbents are used to separate para-xylene from other xylene isomers.

To the extent that the present invention employs as the pre-pulse technique, the introduction of a non-adsorbed species into the adsorption zone of the process, U.S. Pat. No. 3,715,409, issued to Broughton, is believed pertinent. In Broughton '409, there is taught the recycling to the adsorption zone of a stream comprising highly purified raffinate material for the purpose of enhancing process performance. Like the Broughton '409 invention, the pre-pulse technique employed herein concerns the introduction of a non-adsorbed material into the adsorption zone of the process. However, in contradistinction to the Broughton '409 invention, the pre-pulse technique most preferably employed in the process of this invention uses a wholly external stream composed of non-feed material.

In contrast, this invention relates to the adsorptive separation of non-hydrocarbons and more specifically to the separation of one or more hydroxy paraffinic dicarboxylic acids from a feed mixture comprising one or more hydroxy paraffinic dicarboxylic acids and one or more olefinic dicarboxylic acids utilizing therein a hydrophobic, non-zeolitic crystalline silica molecular sieve adsorbent material.

SUMMARY OF THE INVENTION

It has been discovered that silicalite, a non-zeolitic, hydrophobic, crystalline silica molecular sieve material, is particularly suitable for the separation process of this invention in that it exhibits a selectivity for the olefinic dicarboxylic acids (such as fumaric and maleic acids) relative to hydroxy paraffinic dicarboxylic acids (such as malic acid) thereby selectively rejecting the desirable hydroxy paraffinic dicarboxylic acids to a raffinate stream and is thus especially suitable for use in the separation of the components of a maleic acid hydrolysis reaction product mixture, particularly when used with a specific displacement fluid comprising an aqueous ketone, such as aqueous acetone.

Furthermore, the preferred adsorbent used in the process of the present invention does not exhibit reactivity with the feed mixture at separation conditions. Additionally, since the malic acid component of the feed mixture is generally the major constituent of the feed mixture, the use of a malic acid-rejective system also results in a smaller adsorbent requirement than would be the case with a malic acid-adsorptive system, thereby reducing the physical size and corresponding capital cost requirement of a commercial plant.

In order to obtain the greatest utility of the present invention it is preferred that a so-called pre-pulse technique be employed herein. The use of the pre-pulse technique is essential to maximize the performance of the process to the extent that it enhances the adsorption of olefinic dicarboxylic acids, such as maleic and fumaric acid, which in turn results in a purer hydroxy paraffinic dicarboxylic acid raffinate product.

In a preferred embodiment, it has been found that a pre-pulse medium comprising water functions well. It will be noted that the process of the present invention can be practiced without the use of the pre-pulse technique; however, the results are inferior with respect to the ultimate raffinate product stream purity.

Therefore, in one embodiment, the present invention concerns a process for separating hydroxy paraffinic dicarboxylic acids from a feed mixture comprising one or more olefinic dicarboxylic acids and one or more hydroxy paraffinic dicarboxylic acids, utilizing a hydrophobic, non-zeolitic crystalline silica molecular sieve adsorbent material to effect the adsorption of the olefinic dicarboxylic acid components of the feed mixture in preference to the hydroxy paraffinic dicarboxylic acid components of the feed mixture and thereafter recovering a purified amount of the hydroxy paraffinic dicarboxylic acid.

Other embodiments of the present invention encompass details about feed mixtures, adsorbents, desorbent materials, flow schemes and operating conditions all of which are hereinafter disclosed in the following discussion of each of the facets of the present invention.

DESCRIPTION OF THE FIGURES

Figure 1:
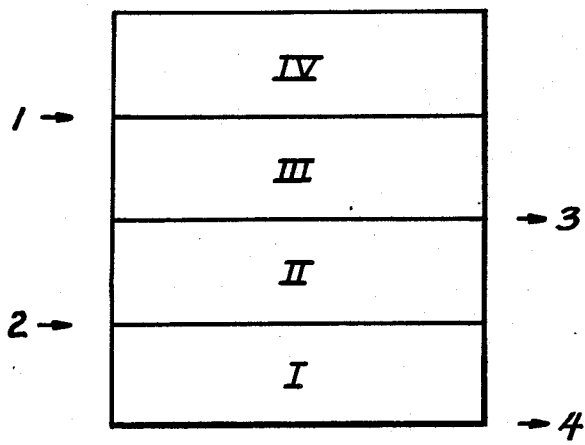
FIG. 1 is a simplified process flow diagram of a countercurrent simulated moving bed separation process configured in accordance with the technique of the prior art.

In FIG. 1, line 1 is the desorbent input to the process; line 2 is the feed to the process; line 3 is the extract product; line 4 is the raffinate product. The portions of the adsorbent vessel labelled I, II, III and IV are, respectively, the adsorption, purification, desorption zones and optional buffer zone of a simulated moving bed separation process of the prior art.

Figure 2:
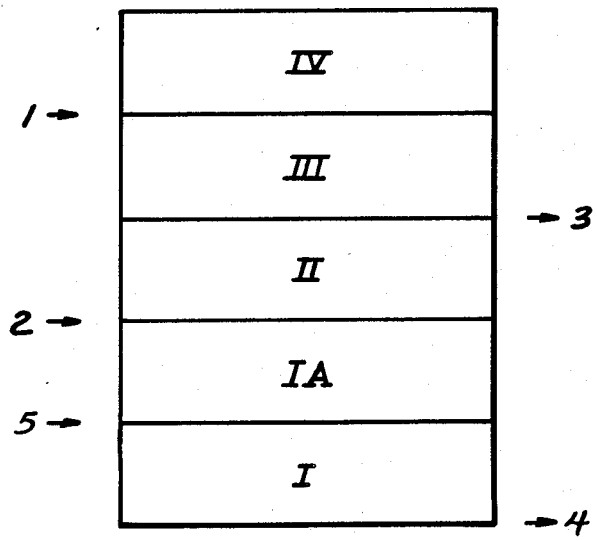
FIG. 2 is a simplified process flow diagram of a countercurrent simulated moving bed separation process employing therein the preferred embodiment of the present invention and showing the general relative location of each zone while employing the pre-pulse technique.

In FIG. 2, line 1 is the desorbent input to the process; line 2 is the feed to the process; line 5 is the pre-pulse input stream; line 3 is the extract product; line 4 is the raffinate product. The portions of the adsorbent vessel labelled I, IA, II, III, and IV are, respectively, the adsorption, pre-pulse, purification, desorption zones and optional buffer zone of a simulated moving bed adsorptive separation process employing the present invention.

DESCRIPTION OF THE INVENTION

At the outset the definitions of various terms used throughout this specification will be useful in making clear the operation, objects and advantages of the process.

A "feed mixture" is a mixture containing one or more extract components and one or more raffinate components to be fed to an adsorbent of the process. The term "feed stream" indicates a stream of feed mixture which passes to an adsorbent used in the process.

An "extract component" is a type of compound or a compound, such as type of dicarboxylic acid that is more selectively adsorbed by the adsorbent while a "raffinate component" is a compound or type of compound that is less selectively adsorbed. In this process, olefinic dicarboxylic acid component(s) of the feed material are the extract component(s) and hydroxy paraffinic dicarboxylic acid components(s) of the feed material are the raffinate component(s). The term "raffinate stream" or "raffinate output stream" means a stream through which a raffinate component is removed from an adsorbent. In the preferred embodiment of the present invention, the raffinate components are the desirable commercial products of the process of the present invention. The composition of the raffinate stream can vary from essentially 100% desorbent material (hereinafter defined) to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. Although it is possible by the process of this invention to produce high-purity extract product (hereinafter defined) or a raffinate product (hereinafter defined) at high recoveries, it will be appreciated that an extract component is never completely adsorbed by the adsorbent, nor is a raffinate component completely non-adsorbed by the adsorbent. Therefore, small amounts of a raffinate component can appear in the extract stream, and, likewise, small amounts of an extract component can appear in the raffinate stream. The extract and raffinate streams then are further distinguished from each other and from the feed mixture by the ratio of the concentrations of an extract component and a specific component, both appearing in the particular stream. For example, the ratio of concentration of the more selectively adsorbed olefinic dicarboxylic acids to the concentration of less selectively adsorbed hydroxy paraffinic dicarboxylic acids will be highest in the extract stream, next highest in the feed mixture, and lowest in the raffinate stream. Likewise, the ratio of the less selectively adsorbed hydroxy paraffinic dicarboxylic acids to the more selectively adsorbed olefinic dicarboxylic acids will be highest in the raffinate stream, next highest in the feed mixture, and the lowest in the extract stream.

The term "pre-pulse input stream" shall mean a stream comprising substantially unadsorbed (i.e., non-olefinic) material such as water. The function of the (water) pre-pulse material in the pre-pulse zone is to locally affect the competition of the components of the liquid which is in contact with the adsorbent in said zone so as to enhance the adsorption of the olefinic dicarboxylic acid components of the feed mixture also present in said liquid due to the relative selectivities of the adsorbent for the olefinic components of the feed and the desorbent material. As the feed material traverses the adsorption zone, incomplete adsorption of the olefinic components of the feed can occur. Specifically, a portion of the olefinic dicarboxylic acids present in the feed mixture are passed over the adsorbent but not adsorbed thereon, resulting in a raffinate product comprising a undesirably high proportion of such olefinic dicarboxylic acids.

It should be mentioned that one alternative to the use of the pre-pulse technique is the use of a "weaker" (e.g., a more dilute aqueous ketone) desorbent material, however, this would also be expected to result in a poorer olefinic dicarboxylic acid desorption rate which, as will be discussed later, is undesirable. Even though such poorer desorption rate may be offset by the use of elevated process temperatures, it is known that higher temperatures can detrimentally affect the equilibrium composition of the feed mixture by promoting the reversion of malic acid to fumaric acid and water.

The term "desorbent material" shall mean generally a material capable of desorbing an extract component. The term "desorbent stream" or "desorbent input stream" indicates the stream through which desorbent material passes to the adsorbent. When the extract stream and the raffinate stream contain desorbent materials, at least a portion of the extract stream and preferably at least a portion of the raffinate stream from the adsorbent will be passed to separation means, typically fractionators, where at least a portion of desorbent material will be separated at separation conditions to produce an extract product and a raffinate product.

The terms "extract product" and "raffinate product" mean products produced by the process containing, respectively, an extract component and a raffinate component in higher concentrations than those found in the respective extract stream and the raffinate stream. The term "selective pore volume" of the adsorbent is defined as the volume of the adsorbent which selectively adsorbs extract components from a feed mixture.

The term "non-selective void volume" of an adsorbent is the volume of an adsorbent which does not selectively retain an extract component from a feed mixture. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into the process for efficient operations to take place for a given quantity of adsorbent. When adsorbent "passes" into an operational zone (which zones are used in a preferred embodiment of this process and are hereinafter defined and described) its non-selective void volume together with its selective pore volume carries fluid into that zone. The non-selective void volume is utilized in determining the amount of fluid which should pass into the same zone in a countercurrent direction to the adsorbent to displace the fluid present in the non-selective void volume. If the fluid flow rate passing into a zone is smaller than the non-selective void volume rate of adsorbent material passing into that zone, there is a net entrainment of liquid into the zone by the adsorbent. Since this net entrainment is a fluid present in non-selective void volume of the adsorbent, it in most instances comprises less selectively retained feed mixture components. The selective pore volume of an adsorbent can, in certain instances, adsorb portions of raffinate material from the fluid surrounding the adsorbent since in certain instances there is competition between extract material and raffinate material for adsorptive sites within the selective pore volume. If a large quantity of raffinate material with respect to extract material surrounds the adsorbent, raffinate material can be competitive enough to be adsorbed by the adsorbent.

Feed mixtures which can be utilized in the process of this invention will comprise mixtures of one or more hydroxy paraffinic dicarboxylic acids and one or more olefinic dicarboxylic acids. These hydroxy paraffinic and olefinic dicarboxylic acids can be characterized by reference to Formulae 1(a) and (b), respectively, below:

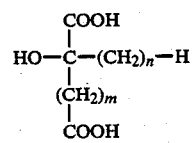

Formula 1(a)

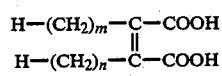

Formula 1(b)

where m and n are whole numbers.

Thus feed mixtures to this process can contain such specific representative compounds as malic, maleic or fumaric acids and combinations thereof. The above list only represents a small fraction of compounds which can be separated by the adsorptive separation process of this invention. Thus the process of this invention may be used for example to separate malic acid from a feed mixture comprising malic, maleic and/or fumaric acids. The most likely separation for employment of the present invention, however, is the separation of malic acid from maleic, fumaric and malic acids.

The feed mixtures may contain small quantities of trace material usually found in commercial feed mixtures, such as organic color bodies, protein, amino acids or carbohydrate. It is preferable to have these quantities at a minimum amount in order to prevent contamination of products from this process by materials which are not selectively adsorbed or separated by the adsorbent. Preferably the above-mentioned contaminants should be less than about 0.01% of the volume of the feed mixture passed into the process.

To separate hydroxy paraffinic dicarboxylic acids from a feed mixture comprising such acids and olefinic dicarboxylic acids, the mixture is contacted with the particular adsorbent and the olefinic dicarboxylic acid(s) is (are) more selectively adsorbed and retained by the adsorbent while the other components of the feed material are relatively unadsorbed and are removed from the interstitial void spaces between the particles of adsorbent and the surface of the adsorbent and passed to a raffinate output stream. The adsorbent containing the more selectively adsorbed components of the feed mixture is referred to as a "rich" adsorbent—rich in the more selectively adsorbed olefinic dicarboxylic acids. The olefinic dicarboxylic acid(s) is (are) then recovered from the rich adsorbent by contacting the rich adsorbent with a desorbent material.

The desorbent materials which can be used in this process will vary depending on the type of operation employed. The term "desorbent material" as used herein shall mean any fluid substance capable of removing a selectively adsorbed feed component from the adsorbent. In the swing-bed system in which the selectively adsorbed feed component is removed from the adsorbent by a purge stream desorbent material, selection is not too critical and desorbent materials comprising gaseous hydrocarbons such as methane, ethane, etc., or other types of gases such as nitrogen or hydrogen may be used at elevated temperatures or reduced pressures, or both, to effectively purge the adsorbed feed component from the adsorbent. However, in adsorptive separation processes which employ zeolitic adsorbents and which are generally operated continuously at substantially constant pressures and temperatures so as to maintain liquid phase, the desorbent material relied upon must be judiciously selected to satisfy several criteria. First, the desorbent material must displace the extract components from the adsorbent with reasonable mass flow rates without itself being so strongly adsorbed as to unduly prevent the extract component from displacing the desorbent material in a following adsorption cycle. As aforesaid, the employment of the pre-pulse technique may compensate somewhat for such detrimental effects of a strong desorbent. Expressed in terms of the selectivity (hereinafter discussed in more detail), it is preferred that the adsorbent be more selective for the extract component with respect to a raffinate component than it is for the desorbent material with respect to a raffinate component. Secondly, desorbent materials must be compatible with the particular adsorbent and the particular feed mixture. More specifically, they must not reduce or destroy the critical selectivity to the adsorbent for the extract components with respect to the raffinate component. Desorbent materials to be used in the process of this invention should additionally be substances which are easily separable from the feed mixture that is passed into the process. After desorbing the extract components of the feed, both desorbent material and the extract components are typically removed in admixture from the adsorbent. Likewise, one or more raffinate components is typically withdrawn from the adsorbent in admixture with desorbent material and without a method of separating at least a portion of desorbent material, such as distillation, neither the purity of the extract product nor the purity of the raffinate product would be very high. It is therefore contemplated that any desorbent material used in this process will have a substantially different average boiling point than that of the feed mixture to allow separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture.

In the preferred isothermal, isobaric, liquid-phase operation of the process of this invention, it has been found that desorbent materials comprising aqueous ketones having average boiling points substantially different from that of a feed mixture meet those requirements and are particularly effective. Especially preferred for this process are desorbent materials comprising aqueous acetone.

The prior art has recognized that certain characteristics of adsorbents are highly desirable, if not absolutely necessary, to the successful operation of a selective adsorption process. Among such characteristics are: adsorptive capacity for some volume of an extract component per volume of adsorbent; the selective adsorption of an extract component with respect to a raffinate component and the desorbent material; and, sufficiently fast rates of adsorption and desorption of the extract components to and from the adsorbent.

Capacity of the adsorbent for adsorbing a specific volume of one or more extract components is, of course, a necessity; without such capacity the adsorbent is useless for adsorptive separation. Furthermore, the higher the adsorbent's capacity for an extract component, the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity, $\beta$, for one component as compared to another component. Relative selectivity can be expressed not only for one feed component as compared to another but can also be expressed between any feed mixture component and the desorbent material. The selectivity, $\beta$, as used throughout this specification is defined as the ratio of the two components of the adsorbed phase over the ratio of the same two components in the unadsorbed phase at equilibrium conditions.

Relative selectivity is shown as Equation 1 below:

Equation 1

$$\text{Selectivity} = \beta \frac{[\text{vol. percent } C/\text{vol. percent } D]_A}{[\text{vol. percent } C/\text{vol. percent } D]_U}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases.

Where selectivity of two components approaches 1.0 there is no preferential adsorption of one component by the adsorbent with respect to the other; they are both adsorbed (or non-adsorbed) to about the same degree with respect to each other. As the $\beta$ becomes less than or greater than 1.0 there is a preferential adsorption by the adsorbent for one component with respect to the other. When comparing the selectivity by the adsorbent of one component C over component D, a $\beta$ larger than 1.0 indicates preferential adsorption of component C within the adsorbent. A $\beta$ less than 1.0 would indicate that component D is preferentially adsorbed leaving an unadsorbed phase richer in component C and an adsorbed phase richer in component D. While separation of an extract component from a raffinate component is theoretically possible when the selectivity of the adsorbent for the extract component with respect to the raffinate component just exceeds a value of 1.0, it is preferred that such selectivity have a value approaching or exceeding 2. Like relative volatility, the higher the selectivity the easier the separation is to perform. Higher selectivities permit a smaller amount of adsorbent to be used in the process. Ideally desorbent materials should have a selectivity equal to about 1 or less than 1 with respect to all extract components so that all of the extract components can be extracted as a class and all raffinate components clearly rejected into the raffinate stream.

The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

In order to test various adsorbents and desorbent material with a particular feed mixture to measure the adsorbent characteristics of adsorptive capacity and selectivity and exchange rate a dynamic testing apparatus is employed. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze "on-stream" the effluent stream leaving the adsorbent chamber.

A pulse test, performed using this apparatus and the following general procedure, is used to determine selectivities and other data for various adsorbent systems. The adsorbent is filled to equilibrium with a particular desorbent by passing the desorbent material through the adsorbent chamber. At a convenient time, if the employment of a pre-pulse technique is desired, a pre-pulse of a suitable pre-pulse material (water, for instance) is injected for a duration of several seconds. Immediately thereafter, a pulse of feed containing known concentrations of a non-adsorbed polysaccharide tracer (Maltrin-150, TM a product of Grain Processing Corporation for instance) and of the particular hydroxy paraffinic and olefinic carboxylic acids all diluted in desorbent is injected for a duration of several minutes. Desorbent flow is resumed, and the tracer and the dicarboxylic acids are eluted as in a liquid-solid chromatographic operation. The effluent can be analyzed by on-stream chromatographic equipment and traces of the envelopes of corresponding component peaks developed. Alternately, effluent samples can be collected periodically and later analyzed separately be gas chromatography.

From information derived from the chromatographic traces, adsorbent performance can be rated in terms of capacity index for an extract component, selectivity for one isomer with respect to the other, and the rate of desorption of an extract component by the desorbent. The capacity index may be characterized by the distance between the center of the peak envelope of the selectively adsorbed dicarboxylic acid and the peak envelope of the tracer component of some other known reference point. It is expressed in terms of the volume in cubic centimeters of desorbent pumped during this time interval. Selectivity, $\beta$, for an extract component with respect to a raffinate component may be characterized by the ratio of the distance between the center of an extract component peak envelope and the tracer peak envelope (or other reference point) to the corresponding distance between the center of a raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

Adsorbents to be used in the process of this invention will comprise non-zeolitic, hydrophobic, crystalline silica molecular sieve materials. The molecular sieve material to be used in the preferred embodiment of this invention comprises silicalite. Silicalite is disclosed and claimed in U.S. Pat. Nos. 4,061,724 and 4,104,294 to Grose et al, incorporated herein by reference. Due to its aluminum-free structure, silicalite does not show ion-exchange behavior, and is hydrophobic and organophilic. Silicalite thus comprises a molecular sieve, but not a zeolite. Silicalite is suitable for the separation process of this invention for the presumed reason that its pores are of a size and shape that enable the silicalite to function as a molecular sieve, i.e., accept the molecules of olefinic dicarboxylic acids into its channels or internal structure, while rejecting the molecules of hydroxy paraffinic dicarboxylic acids. A more detailed discussion of silicalite may be found in the article, "Silicalite, A New Hydrophobic Crystalline Silica Molecular Sieve"; Nature, Vol. 271, Feb. 9, 1978, incorporated herein by reference.

Silicalite, like prior art adsorbents, or molecular sieves, is most advantageously used when associated with an appropriate binder material, particularly an amorphous material having channels and cavities therein which enable liquid access to the silicalite. The binder aids in forming or agglomerating the crystalline particles of the silicalite which otherwise would comprise a fine powder. The silicalite molecular sieve may thus be in the form of particles such as extrudates, aggregates, tablets, macrospheres or granules having a desired particle range, preferably from about 16 to about 60 mesh (Standard U.S. Mesh). It has been also discovered that in the presence of the preferred desorbent material the colloidal amorphous silica is an ideal binder for silicalite in that like the silicalite itself this binder exhibits no reactivity for the free olefinic or hydroxy paraffinic dicarboxylic acids. A preferred silica is marketed by DuPont Co. under the trademark Ludox TM. The silicalite powder is dispersed in the Ludox TM which is then gelled and treated in a manner so as to substantially eliminate hydroxyl groups, such as by thermal treatment in the presence of oxygen at a temperature from about 450° C. to about 1000° C. for a minimum period from about 3 hours to about 48 hours. The silicalite should be present in the silica matrix in amounts ranging from about 75 wt. % to about 98 wt. % silicalite based on volatile free composition.

The adsorbent may be employed in the form of a dense fixed bed which is alternatively contacted with a feed mixture and a desorbent material in which case the process will be only semicontinuous. In another embodiment a set of two or more static beds of adsorbent may be employed with appropriate valving so that a feed mixture can be passed through one or more adsorbent beds of a set while a desorbent material can be passed through one or more of the other beds in a set. The flow of a feed mixture and a desorbent material may be either up or down through an adsorbent in such beds. Any of the conventional apparatus employed in static bed fluid-solid contacting may be used.

Separation processes employing countercurrent moving-bed or simulated moving-bed countercurrent flow systems, however, have much greater separation efficiencies than do separation processes employing fixed adsorbent bed systems. With the moving-bed or simulated moving-bed flow systems a feed mixture and a desorbent material are continuously fed to the process and adsorption and desorption are continuously taking place which allows continuous production of an extract output stream and a raffinate output stream. In a preferred embodiment therefore the process will use such flow systems. In a more preferred embodiment the process will employ a simulated moving-bed countercurrent flow system. The operating principles and sequence of operation of one such simulated moving-bed countercurrent flow system are described in U.S. Pat. No. 2,985,589 incorporated herein by reference. In such a system it is the progressive movement of multiple liquid access points down an adsorbent chamber that simulates the upward movement of an adsorbent contained in the chamber. Only four of the access lines are active at any one time; the feed input stream, desorbent inlet stream, raffinate outlet stream, and extract outlet stream access lines. In the case of the employment of the pre-pulse technique, a fifth stream, the pre-pulse input stream, would also be active. Coincident with this simulated upward movement of a solid adsorbent is the movement of a liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which required different flow rates. A programmed flow controller may be provided to set and regulate these flow rates. Of course, in the practice of the preferred embodiment of the present invention, an additional line, i.e., the pre-pulse input stream, would also be active.

The active liquid access points effectively divide the adsorbent chamber into separate zones, each of which has a different function. In this embodiment of the present process it is generally necessary that three (or if the pre-pulse technique is employed, four) separate operational zones be present in order for the desired operations to take place although in some instances an optional fourth zone may be used.

The adsorption zone, Zone 1, is defined as the adsorbent located between a feed inlet stream and raffinate outlet stream. In this zone, a feed mixture contacts an adsorbent, an extract component is adsorbed, and a raffinate stream is withdrawn. Since the general flow through Zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in Zone 1, is the pre-pulse zone, Zone 1A. The pre-pulse zone is defined as the adsorbent between a feed input stream and a pre-pulse input stream. The basic phenomenon taking place in Zone 1A is the local displacement of desorbent material surrounding the adsorbent particles by the pre-pulse input stream. This results in an increased adsorption of the extract components also surrounding the adsorbent particles. The flow of material in Zone 1A is in a downstream direction.

Immediately upstream with respect to fluid flow in Zone 1A is the purification zone, Zone 2. The purification zone is defined as the adsorbent between an extract outlet stream and the feed inlet stream. The basic operations taking place in Zone 2 are the displacement from the non-selective void volume of the adsorbent of any raffinate material carried into Zone 2 by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving Zone 3 (hereinafter described) into Zone 2 at Zone 2's upstream boundary, the extract outlet stream, to effect the displacement of raffinate material. The flow of material in Zone 2 is in a downstream direction from the extract outlet stream to the feed inlet stream.

Immediately upstream of Zone 2 with respect to the fluid flowing in Zone 2 is the desorption zone or Zone 3. The desorption zone is defined as the adsorbent between a desorbent inlet stream and the extract outlet stream. The function of the desorption zone is to allow a desorbent material which passes into this zone to displace the extract component which was adsorbed upon the adsorbent during a previous contact with feed in Zone 1A in a prior cycle of operation. The flow of fluid in Zone 3 is essentially in the same direction as that of Zones 1A and 2.

In some instances an optional buffer zone, Zone 4, may be utilized. This zone, defined as the adsorbent between the raffinate outlet stream and the desorbent inlet stream, if used, is located immediately upstream with respect to the fluid flow to Zone 3. Zone 4 would be utilized to conserve the amount of desorbent utilized in the desorption step since a portion of the raffinate stream which is removed from Zone 1 can be passed into Zone 4 to displace desorbent material present in that zone out of that zone into the desorption zone.

Zone 4 will contain enough adsorbent so that raffinate material present in the raffinate stream passing out of Zone 1 and into Zone 4 can be prevented from passing into Zone 3 thereby contaminating the extract stream removed from Zone 3. In the instances in which the fourth operational zone is not utilized the raffinate stream passed from Zone 1 to Zone 4 must be carefully monitored in order that the flow directly from Zone 1 to Zone 3 can be stopped when there is an appreciable quantity of raffinate material present in the raffinate stream passing from Zone 1 into Zone 3 so that the extract outlet stream is not contaminated.

A cyclic advancement of the input and output streams through the fixed bed of an adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically rotary disc valves which can be utilized in this operation can be found in U.S. Pat. Nos. 3,040,777 and 3,422,848, incorporated herein by reference. Both of the aforementioned patents disclose a rotary type connection valve in which the suitable advancement of the various input and output streams from fixed sources can be achieved without difficulty.

In many instances, one operational zone will contain a much larger quantity of an adsorbent than some other operational zone. For instance, in some operations the buffer zone can contain a minor amount of an adsorbent as compared to the adsorbent required for the adsorption and purification zones. It can also be seen that when a very efficient desorbent material is used which can easily desorb an extract component from an adsorbent, it is possible that a relatively small amount of adsorbent will be needed in a desorption zone as compared to the adsorbent needed in the buffer zone or adsorption zone or purification zone. It is not required that an adsorbent be located in a single column which is divided into zones, and the use of multiple chambers or a series of columns is also within the scope of this embodiment.

It is not necessary that all of the input or output streams be simultaneously used, and, in fact, in many instances, some of the streams can be shut off while others effect an input or output of material. One apparatus which can be utilized to effect the process of this invention in a preferred embodiment will contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations function intermittently as a conduit through which material passes into or out of the process.

It is contemplated that at least a portion of the extract output stream will pass into a separation means wherein at least a portion of the desorbent material can be separated at separating conditions to produce an extract product containing a reduced concentration of desorbent material. Preferably, but not necessary to the operation of the process, at least a portion of the raffinate output stream will also be passed to a separation means wherein at least a portion of the desorbent material can be separated at separating conditions to produce a desorbent stream which can be reused in the process and a raffinate product containing a reduced concentration of desorbent material. Typically the concentration of desorbent material in the extract product and the raffinate product will be less than about 5 vol. % and more preferably less than about 1 vol. %. The separation means will typically be a fractionation column, the design and operation of which is well known to the separation art.

Reference can be made to D. B. Broughton, in U.S. Pat. No. 2,985,589 and to a paper entitled "Continuous Adsorptive Processing—A New Separation Technique" by D. B. Broughton presented at the 34th Annual Meeting of the Society of Chemical Engineers at Tokyo, Japan on Apr. 2, 1969, for further explanation of the simulated moving bed countercurrent process flow scheme.

Although both liquid and vapor phase operations can be used in many adsorptive separation processes, liquid-phase operation is preferred for this process because of the lower temperature requirements and because of the higher yields of an extract product that can be obtained with liquid-phase operation over those obtained with vapor-phase operation. Adsorption conditions will include a temperature range of from about 40° C. to about 250° C. with about 55° C. to about 65° C. being more preferred so as to materially inhibit the chemical reversion of hydroxy paraffinic dicarboxylic acids to olefinic dicarboxylic acids, and a pressure range of from about atmospheric to about 500 psig (3450 kPa g) with from about atmospheric to about 250 psig (1725 kpa g) being more preferred to insure liquid phase. Desorption conditions will include the same range of temperatures and pressure as used for adsorption conditions.

The size of the units which can utilize the process of this invention can vary anywhere from those of pilot-plant scale (see for example U.S. Pat. No. 3,706,812) to those of commercial scale and can range in flow rates from as little as a few cc an hour up to many thousands of gallons per hour.

The following examples are presented for illustration purposes and more specifically are presented to illustrate the selectivity relationships that make the process of the invention possible. Reference to specific cations, desorbent materials, feed mixtures and operating conditions is not intended to unduly restrict the scope and spirit of the claims attached hereto.

EXAMPLE I

In this experiment a pulse test was performed to evaluate a silicalite adsorbent's ability to separate malic, maleic and fumaric acids with a moderately strong desorbent without the use of the pre-pulse technique. The base material contained a Linde silicalite material and a small portion of amorphous binder material.

The testing apparatus was an adsorbent chamber containing approximately 70 cc of the adsorbent and contained with a temperature-controlled means in order to maintain essentially isothermal operations through the column. For each pulse test the column was maintained at a temperature of 60° C. and a pressure of 100 psig to maintain liquid-phase operations. Liquid chromatographic analysis equipment was attached to the column effluent stream in order to determine the composition of the effluent material at given time intervals. The feed mixture employed for each test contained about 6 vol. % malic acid, 2 vol. % maleic acid and 1 vol. % fumaric acid and 10 vol. % acetone in water. The operations taking place for each test were as follows. The desorbent material was run continuously at a nominal liquid hourly space velocity (LHSV) of 1.0 which amounted to about 1.17 cc per minute feed rate of desorbent. At some convenient time interval the desorbent was stopped and the feed mixture was run for a 10-minute interval at a rate of 1.0 cc per minute. The desorbent stream was then resumed at 1 LHSV and continued to pass into the adsorbent column until all of the feed material had been eluted from the column as determined by observing the chromatograph generated by the effluent material leaving the adsorption column. The sequence of operations usually takes about two hours. The 10 minutes pulse of feed and subsequent desorption may be repeated in sequence as often as is desired. The attached FIG. 3 comprises the chromatographic traces for the organic acids eluted from the column. Selected information derived from these traces is indicated on each attached figure. (In a separate experimental run, Maltrin-150 TM was injected into the column of adsorbent and displaced by water. The column effluent was continuously monitored in order to determine the void volume of the adsorbent bed.) Note that in this example, no pre-pulse material was injected, therefore the column input sequence was desorbent, feed, desorbent. Therefore, in those cases in which the pre-pulse technique is to be employed, the sequence would be desorbent, pre-pulse for several seconds, feed for ten minutes, followed by desorbent. As can be seen from the curves, maleic acid is the second (after fumaric acid) most strongly retained component from the feed mixture, and would, therefore, be the most likely contaminant of the malic acid (raffinate) product.

Figure 3:
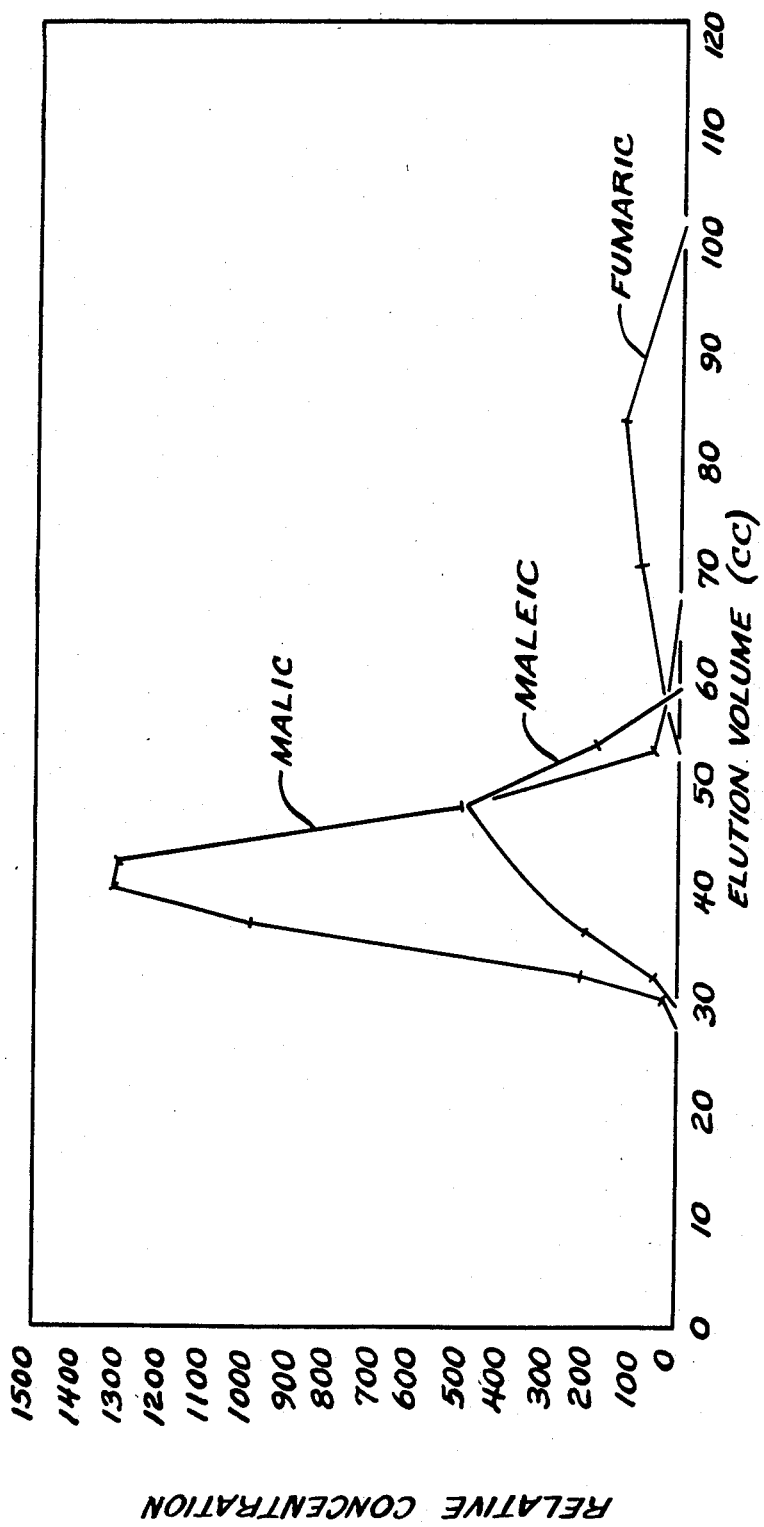
FIG. 3 is a graph of the pulse test of Example I showing the separation of malic, maleic and fumaric acids without using a pre-pulse input stream.

The curves in FIG. 3 show a relatively poor separation achieved for the desorbent used. Almost all of the malic eluted was contaminated with substantial quantities (tailings) of the other components, particularly with maleic acid.

EXAMPLE II

Figure 4:
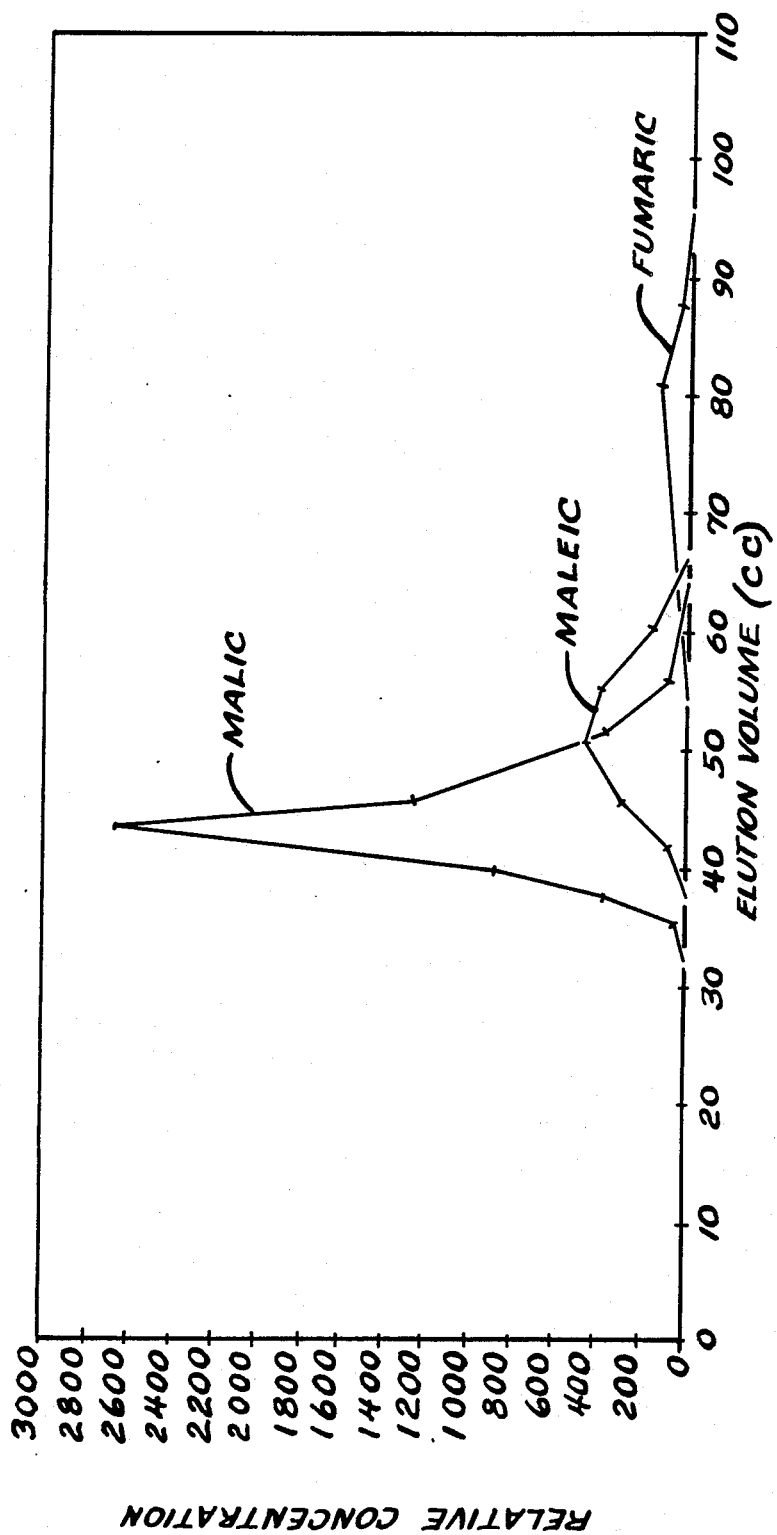
FIG. 4 is a graph of the pulse test of Example II, showing the same separation as Example I except that a pre-pulse input stream was used.

The experiment of Example I was repeated, except that the pre-pulse technique was employed. A pre-pulse medium comprising water was used. Therefore, the column input sequence was desorbent, pre-pulse, feed, desorbent. The results are shown in FIG. 4. The quality of the separation and yield of pure product was markedly better. In fact, not only was the separation between maleic and malic acids more distinct, but the effluent peaks were sharper, indicating an overall faster desorption rate. Thus, the employment of the pre-pulse technique resulted in a marked increase in the selectivity of the adsorbent for olefinic dicarboxylic acids and yield of substantially purer hydroxyl paraffinic dicarboxylic acids.

EXAMPLE III

Figure 5:
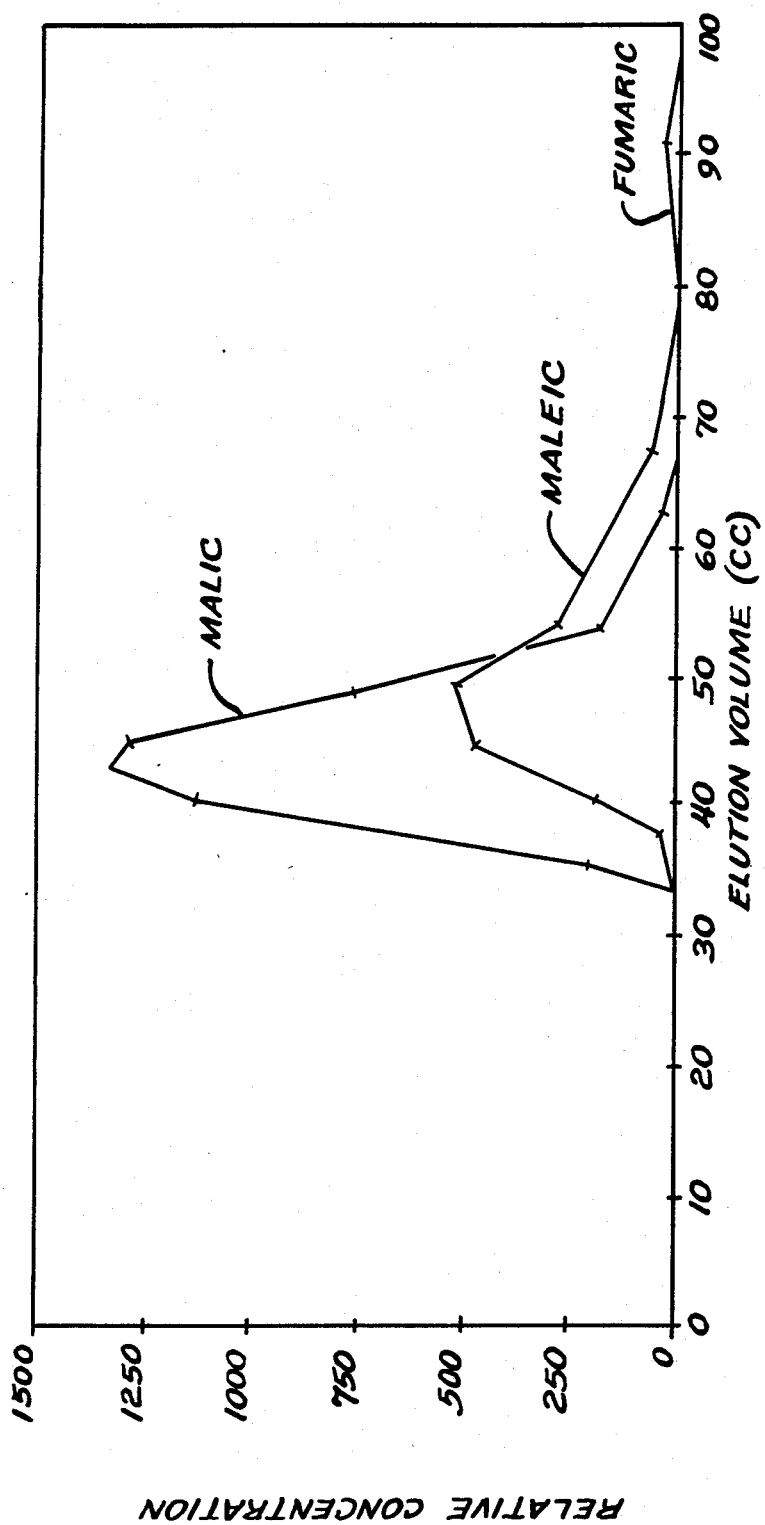
FIG. 5 is like FIG. 3 showing the results of Example III using a weaker desorbent as an alternative to a pre-pulse input stream.

As an alternative to the use of the pre-pulse technique, as aforesaid, a weaker desorbent may be used. To demonstrate this, the experiment of Example I was repeated, except that the desorbent was a more dilute aqueous acetone mixture (i.e., 2 vol. % acetone in water). The results are shown in FIG. 5. Comparing FIGS. 3, 4 and 5, it is clear that the weaker desorbent can achieve some of the results of the pre-pulse technique, however, the malic acid (raffinate) product remains highly contaminated with maleic acid.

What is claimed:

1. A process for separating hydroxy paraffinic dicarboxylic acids from a feed mixture comprising, one or more hydroxy paraffinic dicarboxylic acids and one or more olefinic dicarboxylic acids, which process comprises contacting, at adsorption conditions, said feed mixture with an adsorbent material comprising a hydrophobic, non-zeolitic, crystalline silica, to effect the adsorption of the olefinic dicarboxylic acids and thereby rejecting to a raffinate stream a purified quantity of the hydroxy paraffinic dicarboxylic acids.

2. The process of claim 1 wherein said feed mixture comprises maleic acid, fumaric acid and malic acid.

3. The process of claim 2 wherein said feed mixture results from the hydrolysis reaction of maleic acid.

4. The process of claim 1 wherein the particle size of said adsorbent material is from about 20 to about 40 mesh.

5. The process of claim 1 wherein said adsorbent material comprises silicalite.

6. The process of claim 1 wherein said adsorption conditions include: a temperature within the range of from about 40° C. to about 65° C. so as to materially inhibit the chemical reversion of hydroxy paraffinic dicarboxylic acids to olefinic dicarboxylic acids and a pressure within the range of from about atmospheric to about 500 psig (3450 kPa g) so as to maintain liquid phase.

7. The process of claim 1 wherein the pre-pulse technique is employed comprising the use of a pre-pulse input stream of a non-olefinic nature.

8. The process of claim 7 wherein the pre-pulse input material comprises water.

9. The process of claim 8 wherein the pre-pulse input material consists essentially of water.

10. A process for separating hydroxy paraffinic dicarboxylic acids from a feed mixture comprising, one or more hydroxy paraffinic dicarboxylic acids and one or more olefinic dicarboxylic acids, employing an adsorbent comprising a non-zeolitic, hydrophobic, crystalline silica material, which process comprises the steps of:
(a) maintaining net fluid flow through a column of said adsorbent in a single direction, which column contains at least four zones having separate operational functions occurring therein and being serially interconnected with the terminal zones of said column connected to provide a continuous connection of said zones;
(b) maintaining an adsorption zone in said column, said zone defined by the adsorbent located between a pre-pulse input stream at an upstream boundary of said zone and a raffinate output stream at a downstream boundary of said zone;
(c) maintaining a pre-pulse zone immediately upstream from said adsorption zone, said pre-pulse zone defined by the adsorbent located between a feed input stream at an upstream boundary of said pre-pulse zone and said pre-pulse input stream at a downstream boundary of said pre-pulse zone;
(d) maintaining a purification zone immediately upstream from said adsorption zone, said purification zone defined by the adsorbent located between an extract output stream at an upstream boundary of said purification zone and said feed input stream at a downstream boundary of said purification zone;

(e) maintaining a desorption zone immediately upstream from said purification zone, said desorption zone defined by the adsorbent located between a desorbent input stream at an upstream boundary of said zone and said extract output stream at a downstream boundary of said zone;

(e) passing said feed stream into said pre-pulse zone at adsorption conditions to effect the enhanced, selective adsorption of said olefinic dicarboxylic acids of said feed stream by said adsorbent material in said pre-pulse zone relative to the olefinic constituents of the desorbent material also present in said pre-pulse zone and withdrawing a raffinate output stream from said adsorption zone;

(f) passing said pre-pulse input stream into said adsorption zone at adsorption conditions to effect the further selective adsorption of said olefinic dicarboxylic acids in contact with said adsorbent material by said adsorbent material in said adsorption zone in preference to the components of the desorbent material also in contact with said adsorbent material and withdrawing a raffinate output stream from said adsorption zone comprising a purified amount of the hydroxy paraffinic dicarboxylic acid components of the feed mixture;

(g) passing a desorbent material having a boiling point different than that of the feed mixture to permit separation therefrom by distillation into said desorption zone at desorption conditions to effect the displacement of said olefinic dicarboxylic acids from the adsorbent in said desorption zone;

(h) withdrawing an extract stream comprising said olefinic dicarboxylic acids and desorbent material from said desorption zone;

(i) periodically advancing through said column of adsorbent in a downstream direction with respect to fluid flow in said adsorption zone the pre-pulse input stream, feed input stream, raffinate output stream, desorbent input stream, and extract output stream to effect the shifting of zones through said adsorbent and the production of extract output and raffinate output streams.

11. The process of claim 10 wherein said feed mixture comprises maleic acid, fumaric acid and malic acid.

12. The process of claim 11 wherein feed mixture results from the hydrolysis reaction of maleic acid.

13. The process of claim 10 wherein the particle size of said adsorbent material is from about 20 to about 40 mesh.

14. The process of claim 10 wherein said adsorbent material comprises silicalite.

15. The process of claim 10 wherein said adsorption conditions include: a temperature within the range of from about 40° C. to 65° so as to materially inhibit the chemical reversion of hydroxy paraffinic dicarboxylic acids to olefinic dicarboxylic acids and a pressure within the range of from about atmospheric to about 500 psig (3450 kPa g) so as to maintain liquid phase.

16. The process of claim 10 wherein the pre-pulse technique is employed comprising the use of a pre-pulse input stream of a non-olefinic nature.

17. The process of claim 16 wherein the prepulse input material comprises water.

18. The process of claim 17 wherein the prepulse input material consists essentially of water.

19. The process of claim 10 further characterized in that it includes the step of maintaining a buffer zone immediately upstream from said desorption zone, said buffer zone defined as the adsorbent located between the desorbent input stream at a downstream boundary of said buffer zone and a raffinate output stream at an upstream boundary of said buffer zone.

* * * * *